US00PP37236P2

(12) United States Plant Patent
Holtmaat

(10) Patent No.: US PP37,236 P2
(45) Date of Patent: Jan. 27, 2026

(54) ***RUDBECKIA* PLANT NAMED 'RUDBKST704'**

(50) Latin Name: *Rudbeckia hirta*
Varietal Denomination: RUDBKST704

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/232,186

(22) Filed: Jun. 9, 2025

(30) Foreign Application Priority Data

Sep. 30, 2024 (QZ) ..... 20242271

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

U.S. PATENT DOCUMENTS

PP30,727 P2 * 7/2019 Holtmaat ..... A01H 5/02
Plt./474

* cited by examiner

*Primary Examiner* — Susan Mccormick Ewoldt
(74) *Attorney, Agent, or Firm* — Penny J. Aguirre

(57) ABSTRACT

A new cultivar of *Rudbeckia* plant named 'RUDBKST704' that is characterized by its strong and sturdy stems, its compact plant habit, its single whorl of ray florets per flower, its ray floret colors that are yellow-orange with a lighter and more yellow tips, and its fast propagation and production time and flowers quickly after propagation.

2 Drawing Sheets

Botanical classification: *Rudbeckia hirta*.
Variety Denomination: 'RUDBKST704'.

CROSS-REFERENCE TO RELATED APPLICATIONS

This application claims priority to European Community Plant Variety Office (CPVO) Plant Breeder's Rights Application No. 2024/2271 filed on Sep. 30, 2024, under 35 U.S.C. 119(f), the entire contents of which is incorporated by reference herein. This application is co-pending with a U.S. Plant Patent Applications filed for plants derived from the same breeding program that are entitled *Rudbeckia* Plant Named *Rudbeckia* Plant Named 'RUDBBCH767' (U.S. Plant patent application Ser. No. 19/232,149)*, *Rudbeckia* Plant Named 'RUDLPIR734' (U.S. Plant patent application Ser. No. 19/232,300)* and *Rudbeckia* Plant Named 'RUDBSS851' (U.S. Plant patent application Ser. No. 19/232,228)*.

BACKGROUND OF THE INVENTION

The present invention relates to a new and distinct cultivar of *Rudbeckia hirta* and will hereafter by referred to by its cultivar name, 'RUDBKST704'. The new cultivar is an herbaceous perennial grown for use as a landscape plant.

'RUDBKST704' was selected in July of 2020 by the Inventor from amongst seedlings in a trial field in Zuidwolde, Netherlands. The trial field had been planted with seed derived from open pollination of numerous unpatented and unnamed proprietary plants from the Inventor's breeding program. The collected seeds were pooled before sowing and therefore the parentage is unknown.

Asexual propagation of the new cultivar was first accomplished under the direction of the Inventor by tissue culture using meristematic tissue in Heerhugowaard, The Netherlands in March of 2024. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBKST704' as a unique cultivar of *Rudbeckia*.

1. 'RUDBKST704' exhibits strong and sturdy stems.
2. 'RUDBKST704' exhibits a compact plant habit.
3. 'RUDBKST704' exhibits a single whorl of ray florets per flower.
4. 'RUDBKST704' exhibits ray floret colors that are yellow-orange with a lighter and more yellow tips.
5. 'RUDBKST704' exhibits fast propagation and production time and flowers quickly after propagation.

'RUDBKST704' can be compared to the *Rudbeckia* cultivars 'RUDHT53' (U.S. Plant Pat. No. 30,727) and 'RUDLE169' (U.S. Plant Pat. No. 32,918). 'RUDHT53' is similar to 'RUDBKST704' in having a single whorl of ray florets per inflorescence and in flowering quickly after propagation. 'RUDHT53' differs from 'RUDBKST704' in having smaller plant size, inflorescences that are smaller in size, and ray floret colors that are lighter yellow with more orange at the tip. 'RUDLE169' is similar to 'RUDBKST704' in having a single whorl of ray florets per flower and a similar plant height. 'RUDLE169' differs from 'RUDBKST704' in having ray floret colors that are overall yellow with the upper $3/5^{th}$ portion yellow-orange, a slower propagation and production time, and a slower time to flower after propagation.

'RUDBKST704' can also be compared to the co-pending cultivars of *Rudbeckia*, 'RUDBBCH767', 'RUDLPIR734', and 'RUDBSS851'. 'RUDBBCH767' differs from 'RUDBKST704' in having four whorls of ray florets that are golden yellow in color. 'RUDLPIR734' differs from 'RUDBKST704' in having bi-color flowers. 'RUDLPIR851' differs from 'RUDBSS704' in having semi-double flowers, a flower disc that is fully covered by ray florets, and ray floret colors that are deeper yellow with yellow-orange flushed apexes.

BRIEF DESCRIPTION OF THE DRAWINGS

The accompanying color photographs illustrate the overall appearance and distinct characteristics of the new *Rudbeckia*. The photographs were taken of a 3-month-old plant of 'RUDBKST704' as grown outdoors in a 19-cm container in Zuidwolde, The Netherlands.

The photograph in FIG. 1 is a side view of 'RUDBKST704' in bloom.

Figure 1:
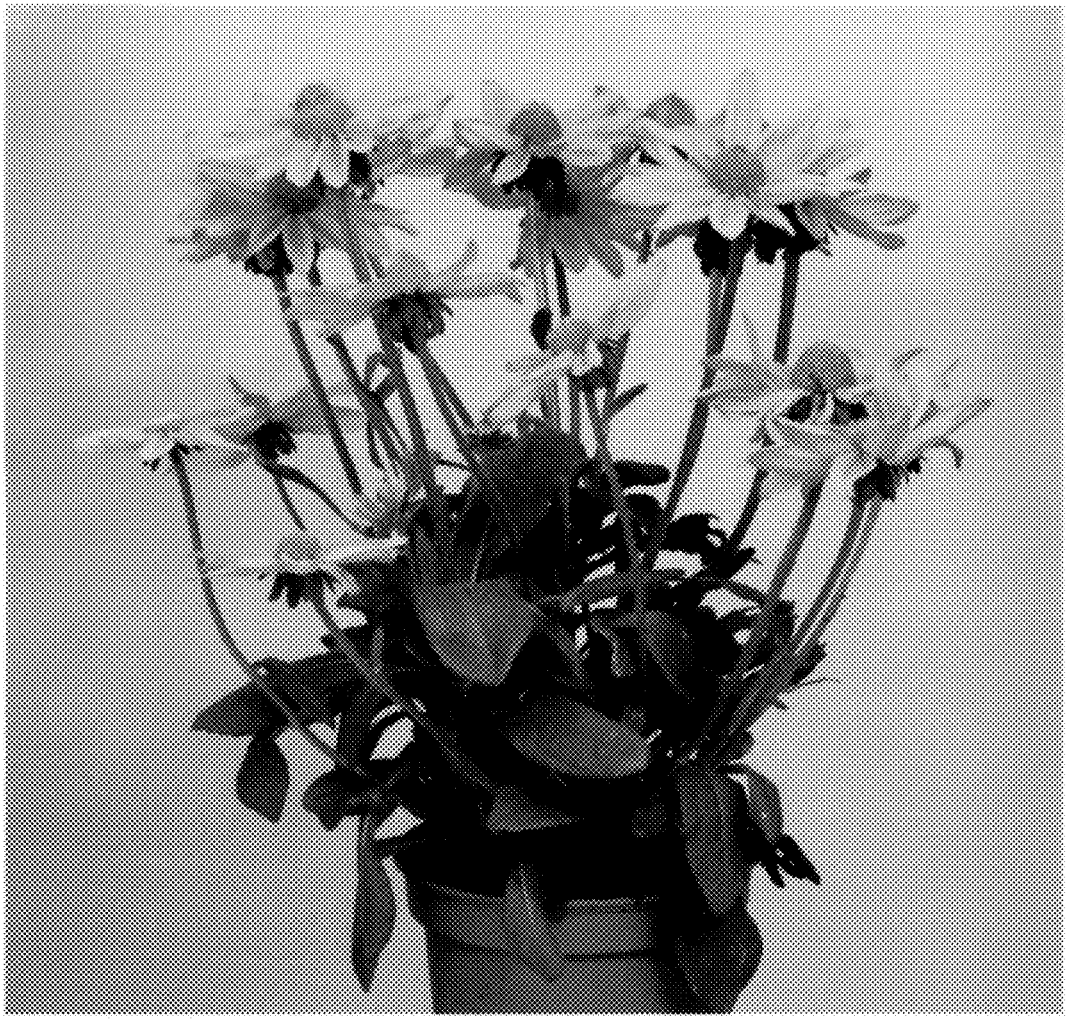
Figure 2:
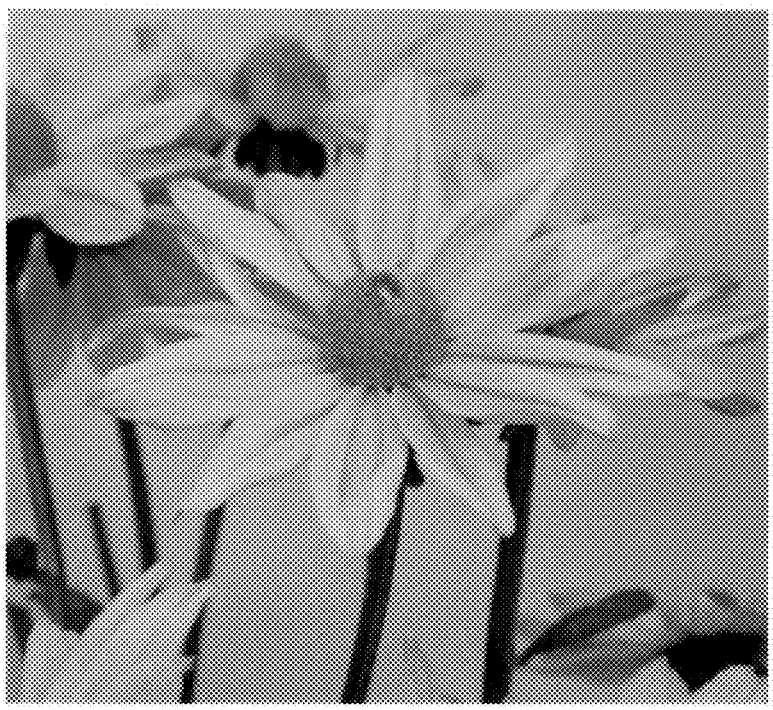

The photograph in FIG. 2 provides a close-up view of an inflorescence of 'RUDBKST704'.

Figure 3:
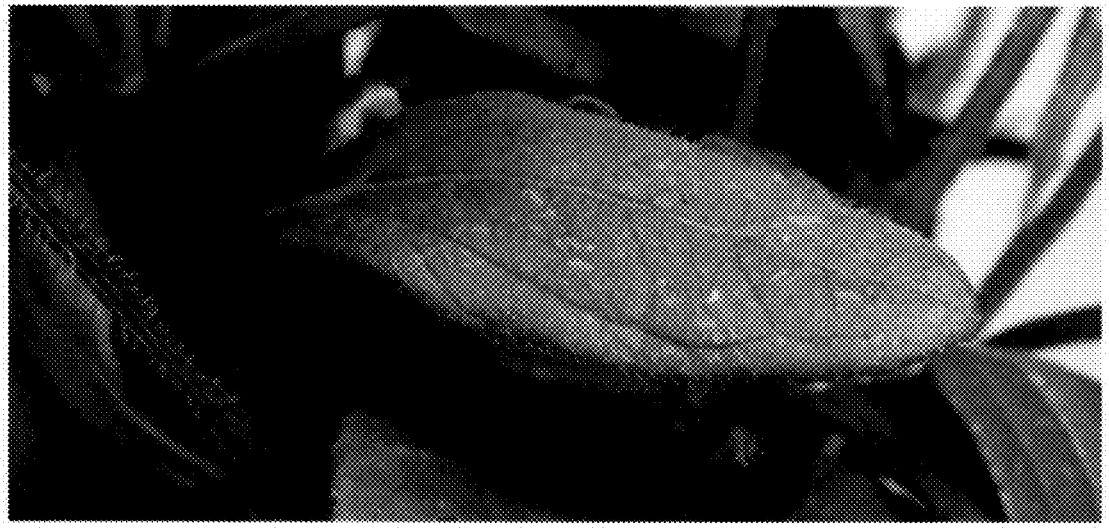

The photograph in FIG. 3 provides a close-up view of a leaf of 'RUDBKST704'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 3-month-old plants of 'RUDBKST704' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 (2019 reprint) Colour Chart of The Royal Horticultural Society, London, England, except where general color terms of ordinary dictionary significance are used.

General description:

*Blooming period*.—June to July in The Netherlands.

*Plant type*.—Perennial.

*Plant habit*. Upright, compact.

*Plant shape*.—Broadly obovate.

*Height and spread*.—Average of 31.2 cm in height from soil level to top of foliar plane and 43.5 cm in height from soil level to top of floral plane, and 46 cm in diameter as a 3-month-old plant grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Vigorous.

Stem description:

*Shape*.—Very slightly angled, 5-sided.

*Stem color*.—Young stems; 144A, mature stems; 143A, slightly darker at angles 144A.

*Stem size*.—An average of 5 mm in diameter and an average of 15.6 cm in length.

*Stem surface*.—Moderately glossy and densely covered with strigose hairs an average of 2 mm in length and N155A in color.

*Stem number*.—Average of 6 main stems, 3 lateral branches per main stem.

*Internode length*.—An average of 3.1 cm in length.

*Stem aspect*.—Main stems; average of 30° to vertical, lateral branches; average of 20° to main stems.

*Branching*.—Freely branching from base with lateral stems.

Foliage description:

*Leaf shape*.—Obovate to narrow obovate.

*Leaf division*.—Simple.

*Leaf base*.—Long cuneate.

*Leaf apex*.—Acute.

*Leaf venation*.—Pinnate, color upper surface 147C, color lower surface 146A.

*Leaf margins*.—Coarsely shallowly crenate-serrate, coarsely slightly undulate.

*Leaf attachment*.—Petiolate.

*Leaf arrangement*.—Alternate.

*Leaf size*.—Average of 11.4 cm in length and 5.2 cm in width.

*Leaf color*.—Young upper surface; 143A, young lower surface; a blend of 138A and 146B, mature upper surface; 137B, mature lower surface; 146B.

*Leaf surface*.—Upper surface very slightly glossy, lower surface slightly glossy, both surfaces rough to the touch, densely pubescent with short strigose hairs; an average of 2 mm in length and N155A in color.

*Petioles*.—Average of 8 mm in length, flattened, average diameter at widest point 9 mm and at narrowest point 4 mm, upper and lower surface color; 144B and 144C, both surfaces slightly glossy and densely covered with strigose hairs; an average of 2 mm in length and N155A in color.

Flower description:

*Type*.—Terminal capitulum, consisting of ray florets and disc florets.

*Capitulum number*.—2 per stem, up to 30 per plant.

*Lastingness of inflorescence*.—Average of 2 weeks, persistent.

*Capitulum size*.—Matures to about 1.7 cm in height and 1.5 cm in diameter, disc size is an average of 2.5 cm in diameter.

*Fragrance*.—None.

*Involucral bracts* (*phyllaries*).—Cuneate base, bluntly acute apex, narrow oblong in shape, entire margins, average of 26 arranged in 2 rows, rotate, slightly curved downward in an angle of −70°, 2 cm in length and 7 mm in width, color; upper surface when fully open 137B, lower surface when fully open 143B, upper surface is very slightly glossy, lower surface is matte, all surfaces including margins are moderately covered with strigose hairs; an average of 2 mm in length and NN155A in color. Receptacle.—Ovate in shape, an average of 1.7 cm in height, 1.5 cm in diameter, 157B in color.

*Buds*.—Shape; flattened globular, immature ray florets pointed upward and slightly curled inwards, involucral bracts nearly horizontal with tips curved downward, 2 cm in length, width; excluding involucral bracts 1.6 cm, including involucral bracts 3.5 cm, color; immature ray florets 151C, upper side of immature involucral bracts 137A, under side of immature involucral bracts 146A to 146B. surfaces are matte and densely covered with strigose hairs; on immature ray florets 1 mm in length of hairs and 150D in color, on involucral bracts 2 m in length and N155A in color.

*Peduncle*.—Strong, straight on top of main flowering stem, average of 18.2 cm in length and 5 mm in diameter, color; 143C, surface moderately glossy and densely covered with short strigose hairs; an average of 1.5 mm in length and N155A in color.

*Ray florets*.—Average of 17, rotate around the disc in 1 row (whorl), oblong to narrow elliptic in shape, average of 5.8 cm in length and 2.3 cm in width, praemorse apex, cuneate base, entire margins, upper surface glabrous and velvety, lower surface densely covered with very short hairs; 0.6 mm in length and 4D in color, held in an average aspect of 20°, color; when opening upper surface 14A, lower half 17A, when opening lower surface 153D, when fully open upper surface 23A, tip a blend of 14A and 15A, veins 151B, when opening lower surface 14B, tip 12A, veins 151B.

*Disc flowers*.—Average of 1,000, 20 whorls arranged spirally on a conical receptacle, lower 90% fused into tube, tubular, upright, 9 mm in length and 3 mm in width, tubular, upper 10% free, free lobes have entire margins, apices of free lobes acute and curled backwards, both surfaces glabrous and slightly glossy, color; when opening upper and lower surface 155C, tip 151B, when fully open upper and lower surface 155C, free lobes at the tip 153D, no spines, but a single bract is placed beside each disc floret; 1 per disc floret, flattened, an average of 8 mm in length and 1.5 mm in diameter, oblanceolate in shape, acute apex, narrowly cuneate base, color; apex 150B, mid-section 145C, base 155C, matte surface and moderately pubescent with hairs; an average of 0.2 mm in length, 150B in color.

Reproductive organs:

*Gynoecium*.—Pistil; 1, 7 mm in length, style; 3 mm in length, 155A in color, stigma; cleft, decurrent, 3 mm in diameter, 153D in color, ovary; 155A in color.

*Androecium*.—Stamens; 5, filaments; 2 mm in length, 155A in color, anther; narrow oblong in shape, 3 mm in length, 0.5 mm in width, 200A in color, pollen; moderate in quantity and 15A in color.

*Fruit/seed*.—None observed to date.

It is claimed:

1. A new and distinct cultivar of *Rudbeckia* plant named 'RUDBKST704' substantially as herein illustrated and described.

* * * * *